United States Patent
Rehil

(12) 
(10) Patent No.: US 6,436,030 B2
(45) Date of Patent: Aug. 20, 2002

(54) HIATAL HERNIA REPAIR PATCH AND METHOD FOR USING THE SAME

(76) Inventor: Om P. Rehil, 821 N. Western Ave., Marion, IN (US) 46952

( * ) Notice: Subject to any disclaimer, the term of this patent is extended or adjusted under 35 U.S.C. 154(b) by 64 days.

(21) Appl. No.: 09/752,771

(22) Filed: Jan. 3, 2001

Related U.S. Application Data

(60) Provisional application No. 60/179,149, filed on Jan. 31, 2000.

(51) Int. Cl.$^7$ .................................................. A61F 2/00
(52) U.S. Cl. ............................ 600/37; 606/151; 623/12
(58) Field of Search ........................... 600/37; 606/151; 623/11, 12

(56) References Cited

U.S. PATENT DOCUMENTS

| | | |
|---|---|---|
| 3,875,928 A | 4/1975 | Angelchik |
| 4,271,827 A | 6/1981 | Angelchik |
| 4,403,604 A | 9/1983 | Wilkinson et al. |
| 4,796,603 A | 1/1989 | Dahlke et al. |
| 5,006,106 A | 4/1991 | Angelchik |
| 5,246,456 A | 9/1993 | Wilkinson |
| 5,290,217 A | * 3/1994 | Campos ........................ 600/37 |
| 5,316,543 A | * 5/1994 | Eberbach ...................... 600/37 |
| 5,634,931 A | 6/1997 | Kugel |
| 5,813,975 A | * 9/1998 | Valenti ........................ 600/37 |
| 5,824,082 A | 10/1998 | Brown |
| 5,861,036 A | 1/1999 | Godin |
| 5,919,233 A | 7/1999 | Knopf et al. |

FOREIGN PATENT DOCUMENTS

WO  WO 91/01117  2/1991

\* cited by examiner

*Primary Examiner*—John P. Lacyk
(74) *Attorney, Agent, or Firm*—Richard C. Litman

(57) ABSTRACT

This invention relates to a surgical prosthesis and method of use. The hiatal hernia repair patch is a ring with an integral mesh attached to and surrounding the ring. The ring and the mesh have a slit therein extending radially so that the ring may be placed about the esophagus. The ring may be hollow or solid and is flexible so that it may be inserted through a small incision or a laparoscopic port into the abdominal cavity. The patch, including the ring and mesh, is made as a one-piece unit and is made from polypropylene or other biocompatible material. In use, the ring is placed around the esophagus, between the stomach and the diaphragm. Next, the mesh is stapled or sutured to the undersurface of the diaphragm, bridging the hiatal hernia defect.

18 Claims, 6 Drawing Sheets

HIATAL HERNIA REPAIR PATCH AND METHOD FOR USING THE SAME

CROSS-REFERENCE TO RELATED APPLICATION

This application claims the benefit of U.S. Provisional Patent Application Serial No. 60/179,149, filed Jan. 31, 2000.

BACKGROUND OF THE INVENTION

1. FIELD OF THE INVENTION

The present invention relates to a method, and a prothesis, for use in maintaining the intra-abdominal reduction of a sliding esophageal hiatal hernia.

2. BACKGROUND OF INVENTION AND DISCUSSION OF RELATED ART

In humans, there is no anatomical valve, or discrete sphincter at the esophago-gastric (EG) junction. When anatomy in the area is normal, esophageal peristalsis pushes food through the EG junction. The stomach fills, like a sack, pulling the EG junction tighter. Normal, intact esophageal hiatal muscles prevent reflux. However, a gaping hiatal muscle sling creates a large defect around the esophagus, thereby interfering with the EG junction mechanism. This may lead to a hiatal hernia.

Anatomically, hiatal hernia is a muscular defect in the diaphragm. The upper part of the stomach migrates through the defect, into the chest, or lower mediastinum. Here, negative pressure leads to free reflux of the stomach's acid into the esophagus. This reflux leads to an array of related symptoms and complications.

Patients afflicted with hiatal hernia suffer immensely. Immediate problems include: severe heartburn, retrosternal pain and burning, and difficulty swallowing. At some point, esophageal ulceration and stricture commonly occur.

Methods and prostheses aimed at repairing hiatal hernias have been the subject of earlier patents. The prior art, discussed below, illustrates previous developments.

Several patents teach the placement of a prosthesis around the esophagus to prevent the stomach from entering the esophagus, or as an anti-reflux measure to prevent reflux of the stomach contents into the esophagus. The placement of a collar or other prosthetic device around the esophagus is sometimes used as an adjunct to hiatal hernia repair procedures in lieu of fundoplication procedures, such as the Nissen fundoplication.

U.S. Pat. No. 3,875,928, issued on Apr. 8, 1975, to Pierre Angelchik, discloses the placement of a C-shaped cushion around the distal esophagus, the cushion having flexible tape at the ends which is tied and then sutured to the gastric fundus. The cushion is filled with a deformable liquid gel and is positioned between the gastric fundus and the diaphragm. The cushion is coated with a radiopaque dye for visualizing the position of the cushion after emplacement on the distal esophagus. The patent fails to mention a means of attachment of the cushion to the diaphragm.

U.S. Pat. No. 4,271,827, issued on Jun. 9, 1981 to Angelchik, discloses a similar prosthesis. This second patent differs only in that it teaches placement above the diaphragm, and in that it teaches securing the patent only by tying the ends of the tape without suturing the cushion to surrounding tissue. Otherwise, the second Angelchik patent has all the limitations of his first. Both of these devices require opening the abdominal or thoracic cavity for placement of the cushion, being unsuited to laparoscopic techniques due to the incompressible liquid or gel filling the cushion.

U.S. Pat. No. 5,006,106, issued Apr. 9, 1991 to Angelchik, discloses a C-shaped cushion with an outer integument of silicone elastomer filled with normal saline solution or hydrogel. A spring is enclosed within and secured to the outer wall of the cushion, the spring having shoulders at its ends so that the spring may be engaged by the tines of laparoscopic forceps. The spring may be made of titanium for radiographic visualization of cushion placement, or made of plastic incorporating a barium compound. The fluid may not be inserted into the cushion until after placement of the integument and spring about the esophagus. The cushion is not sutured or secured to the surrounding tissue.

Other patents directed to preventing the occurrence or recurrence of hiatal hernia include: U.S. Pat. No. 4,796,603, issued on Jan. 10, 1989, to Dahlke et al. (pad made of resorbable material wrapped around the esophagus); U.S. Pat. No. 5,861,036, issued Jan. 19, 1999 to N. Godin (tube extending from esophago-gastric opening into stomach to extend the length of the esophagus and act as a valve, the tube having an annular flange sutured to the basis of a hiatal hernia or the esophagus) ; U.S. Pat. No. 5,919,233, issued on Jul. 6, 1999, to Knopf et al. (flexible, elongated cylinder having a flattened end with a hole in it, the cylinder being wrapped around the esophagus with the free end of the cylinder being inserted through the hole to secure the device to the esophagus); and International Patent No. WO 91/01117, published Feb. 7, 1991 (tubular anti-reflux valve inserted in the esophagus at the level of the hiatal hernia). All teach prostheses that are allowed to move freely around the distal esophagus, or tubes or valves inserted into the esophagus or stomach. All fail to mention a means for attaching the protheses to the diaphragm.

U.S. Pat. No. 4,403,604, issued Sep. 13, 1983 to Wilkinson et al., shows a gastric pouch having mesh panels made of Teflon, Dacron or polypropylene, including a mesh panel wrapped around the junction of the esophagus with the stomach, the pouch being wrapped around the stomach to prevent distention of the stomach and limit the stomach's capacity in order to treat obesity. U.S. Pat. No. 5,246,456, issued Sep. 21, 1993 to L. H. Wilkinson, describes a modification to the pouch due to inability to remove the pouch of the '604 patent because of tissue growth through the mesh. The pouch of the '456 patent is a sheet having holes punched through it, the pouch having a collar made of silicone elastomer with a slit in it for fitting around the esophagus to prevent herniation of the stomach through the hiatal opening in the diaphragm. It will be noted that the curvature of the stomach is inverted by a Nissen fundoplication before wrapping the pouch of both the '604 and '456 patents around the stomach, a procedure which the present invention is designed to avoid.

Hernia mesh patches made from polypropylene, Prolene, or Marlex (made by Phillips Petroleum) have been used for the repair of inguinal hernias and other hernias of the abdominal wall. Representative devices are shown in U.S. Pat. No. 5,634,931, issued Jun. 3, 1997 to R. D. Kugel, and U.S. Pat. No. 5,824,082, issued Oct. 20, 1998 to R. B. Brown. No device using a hernia mesh patch made from polypropylene for the repair of a hiatal hernia is known to applicant.

None of the above inventions and patents, taken either singly or in combination, is seen to describe the instant invention as claimed.

SUMMARY OF THE INVENTION

This invention relates to a surgical prosthesis and method of use. The hiatal hernia repair patch is a ring with an integral mesh attached to and surrounding the ring. The ring and the mesh have a slit therein extending radially so that the ring may be placed about the esophagus. The ring may be hollow or solid and is flexible so that it may be inserted through a small incision or a laparoscopic port into the abdominal cavity. The patch, including the ring and mesh, is made as a one-piece unit and is made from polypropylene or other biocompatible material. In use, the ring is placed around the esophagus, between the stomach and the diaphragm. Next, the mesh is stapled or sutured to the undersurface of the diaphragm, bridging the hiatal hernia defect.

The invention concerns the reconstruction, and reinforcement of the esophago-gastric (EG) junction. Helping the EG junction perform properly controls gastro-esophageal reflux. It also prevents the stomach from migrating into the lower mediastinum, thereby eliminating hiatal hernia.

Accordingly, it is a principal object of the invention to repair a hiatal hernia by implanting a hiatal hernia repair patch which reinforces the esophago-gastric junction, reconstructing the anatomy and stabilizing the esophago-gastric junction, thereby helping it to perform properly.

It is another object of the invention to attach a lightweight prosthesis to the diaphragm which reinforces the junction between the esophagus and the gastric region.

It is a further object of the invention to produce a prosthesis for the repair of a hiatal hernia that allows surrounding tissue to grow into its supporting framework.

It is an object of the invention to provide improved elements and arrangements thereof in a prosthesis for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to a surgical prosthesis, and method for its use, and more specifically to a hiatal hernia repair patch, and the surgical procedure for implanting the patch. The hiatal hernia repair patch will first be discussed with reference to FIG. 1.

Figure 1:
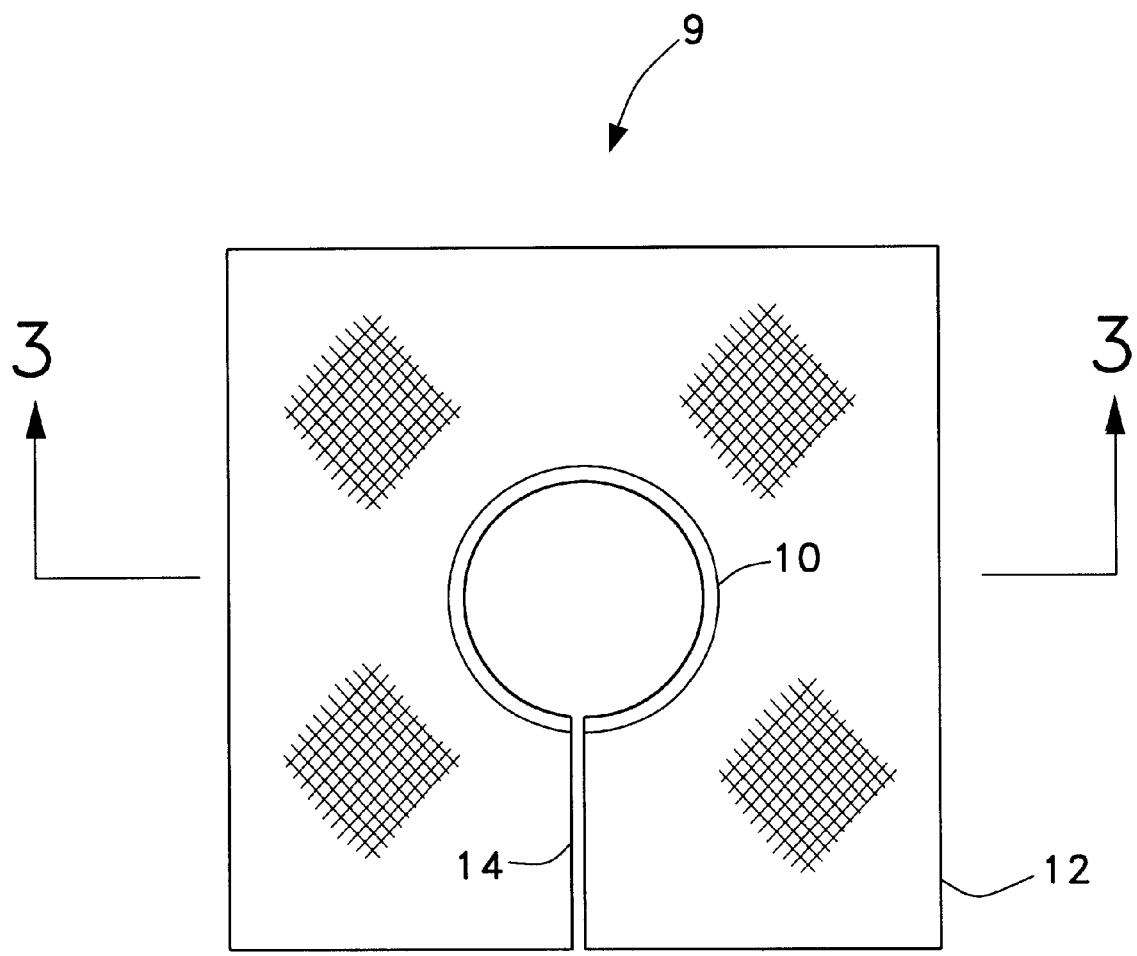
FIG. 1 is a top plan view of a hiatal hernia repair patch according to the present invention.
Figure 5:
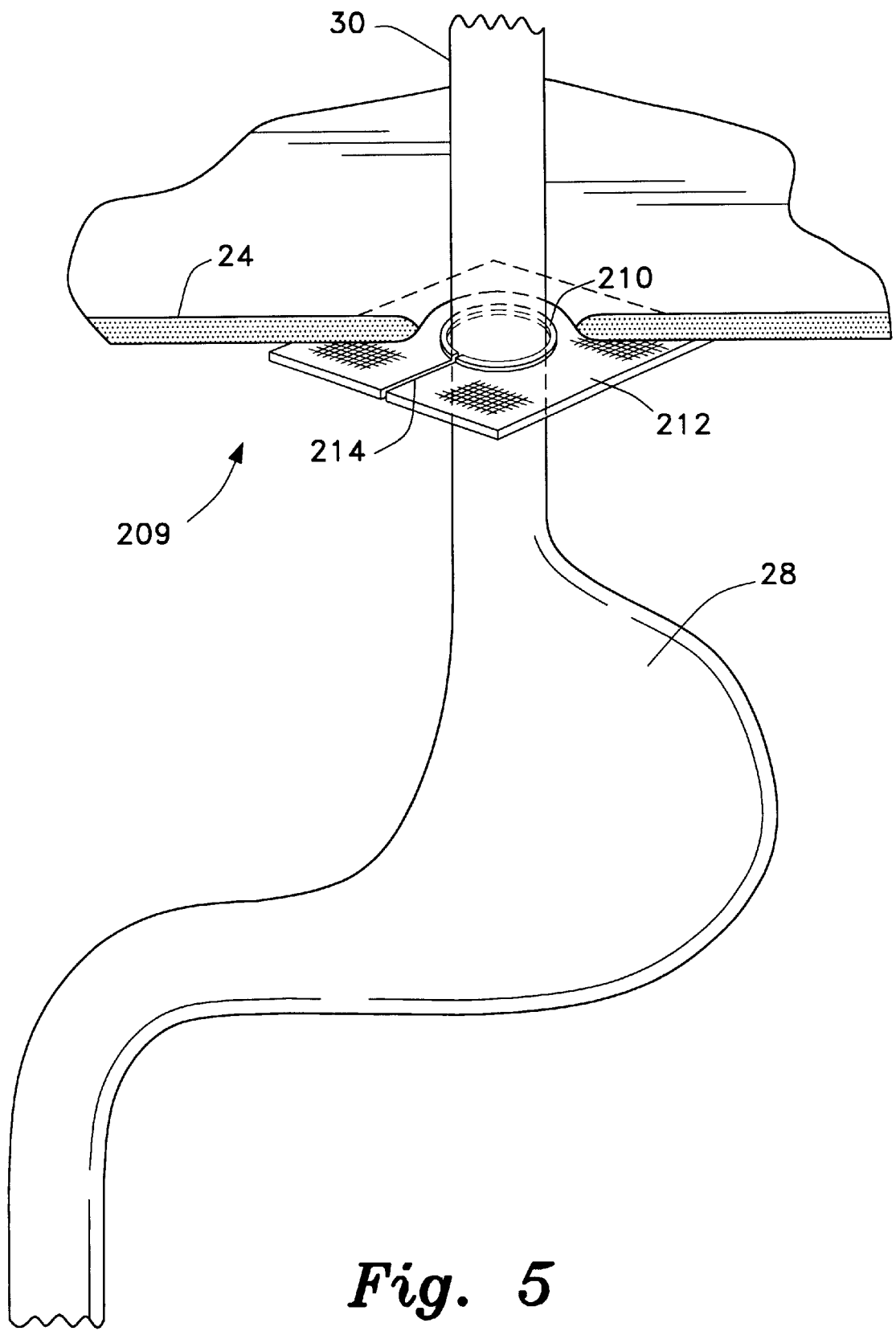
FIG. 5 is an environmental, perspective view of a third embodiment of a hiatal hernia repair patch according to the present invention.

The patch, designated generally as 9 in FIG. 1, comprises a ring 10, surrounded by a piece of biocompatible mesh 12. The diameter of the ring 10, measured from the inside, is generally sized and dimensioned for encircling a patient's distal esophagus. Preferably the mesh 12 extends substantially 360° about the ring 10; however, it will be understood that the scope of the present invention extends to any hernia patch having a ring 10 with a mesh 12 extending radially therefrom, regardless of the pattern of the mesh 12, e.g., the mesh 12 may extend radially from the ring 10 at angular intervals. A single slit 14 in the ring 10 extends radially to and through the surrounding mesh 12. The slit 14 allows placement of the patch 9 around the esophagus 30, as shown in FIG. 5. The mesh 12 may be stapled or sutured to the undersurface of the diaphragm 24 to secure the patch 9. The patch 9 is made from a synthetic biocompatible material, preferably polypropylene, although the patch 9 may be made from other biocompatible material, such as polytetrafluoroethylene (PFTE) Preferably the mesh 12 is attached to the ring 10 by ultrasonic welding, adhesive, molding, or other joining or plastic forming techniques so that the mesh 12 is integral with the ring 10.

Figure 2:
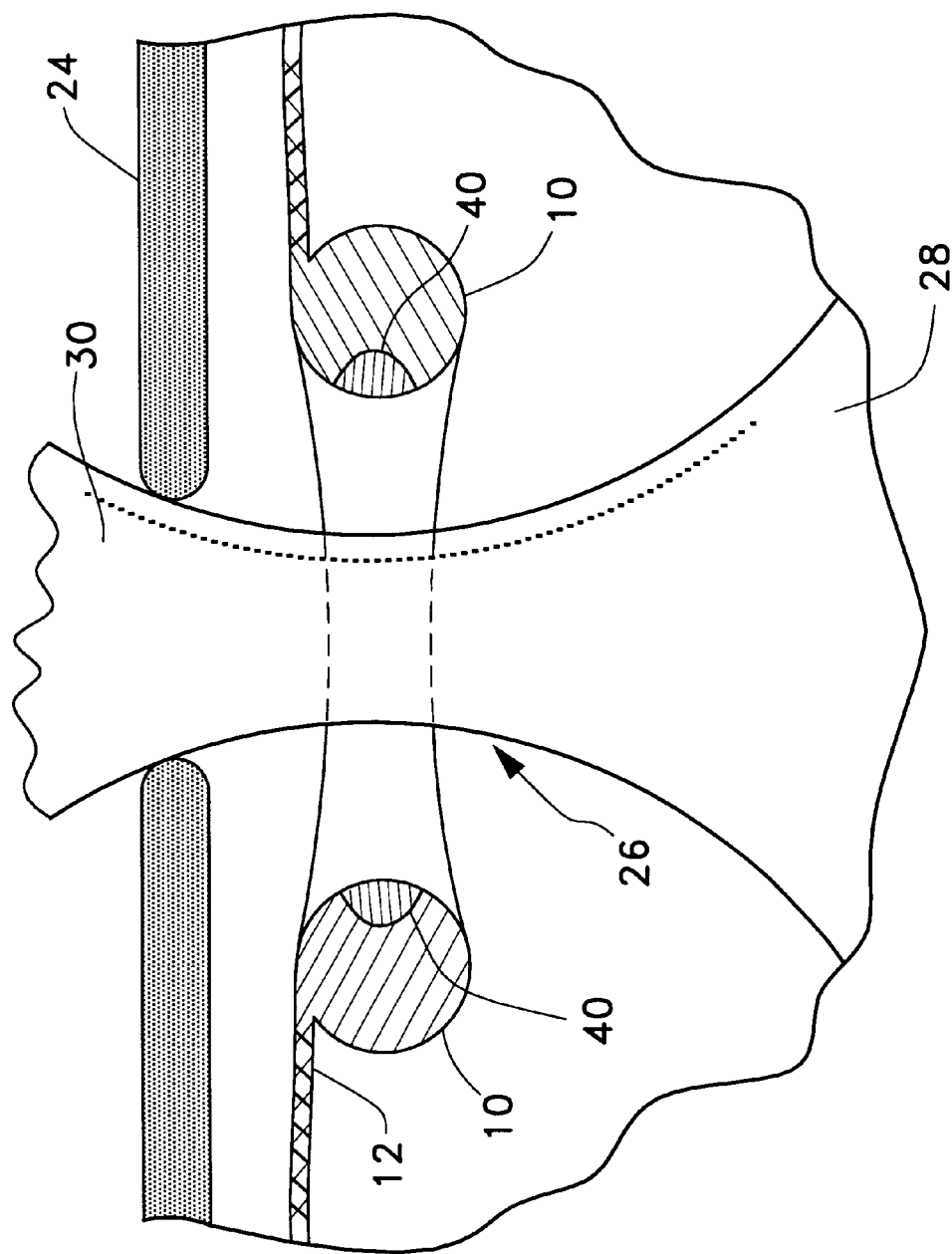
FIG. 2 is an diagrammatic cross-sectional view of a hiatal hernia repair patch according to the present invention showing positioning of the patch.
Figure 3:
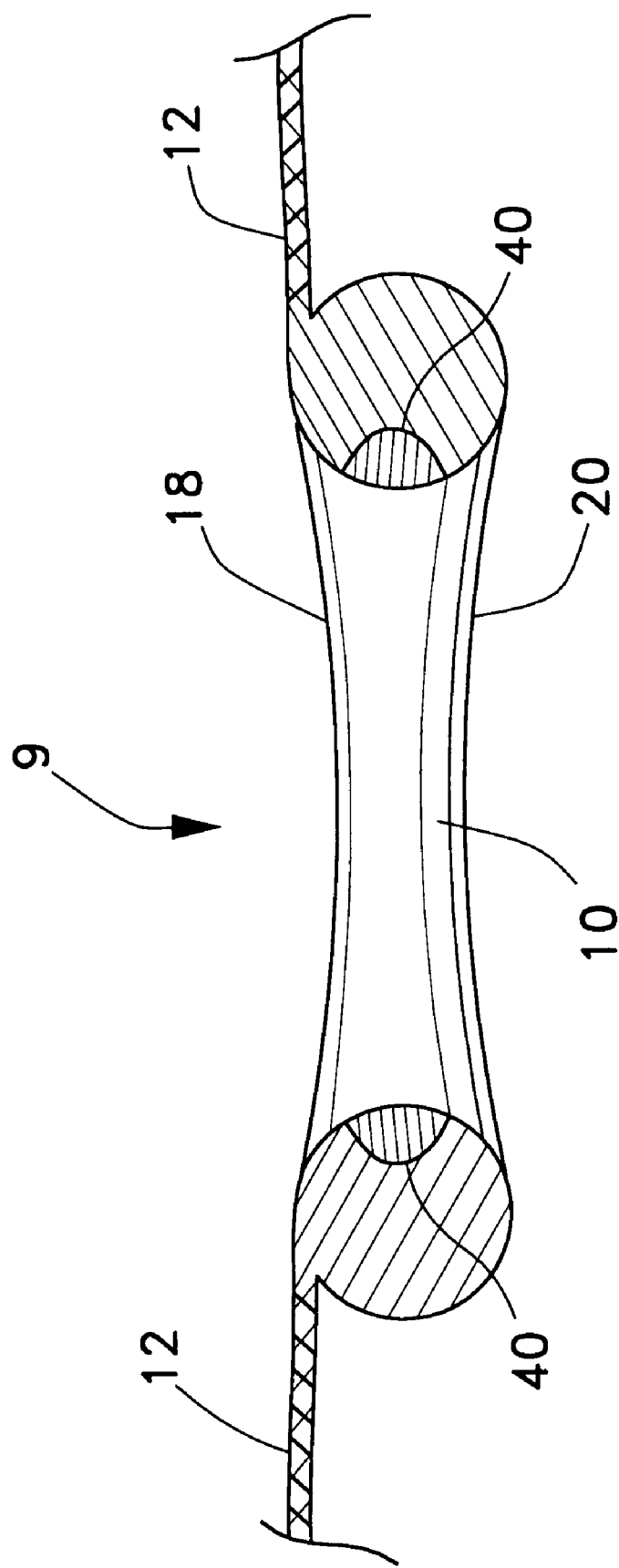
FIG. 3 is a section view along the lines 3—3 of FIG. 1.

FIG. 2 depicts a diagrammatic, close-up, cross-sectional view of the patch 9, illustrating positioning of the patch 9. As shown in FIGS. 2 and 3, the ring 10 is preferably circular in cross-section, with the mesh 12 extending tangentially from one side of the ring 10 rather than extending medially. The patch 9 is implanted with the mesh 12 oriented superiorly and the body of the ring 10 depending inferiorly. Thus, the patch 9 may be referred to as having a superior side 18 and an inferior side 20.

After implantation, surrounding tissue may grow into the mesh 12. As a desirable consequence, this ingrowth further secures the ring 10 to the diaphragm 24. As previously noted, the internal diameter of the ring 10 is selected to closely approximate the diameter of the patient's esophagus at the esophago-gastric (EG) junction. The flexibility of the polypropylene ring 10, as well as the slit 14, permits the ring 10 to expand and contract during normal swallowing, while the mesh 12 restricts movement of the ring 10 up and down the esophagus 30. By strengthening the EG junction 26, the ring 10 prevents the stomach 28 from migrating through the hiatal opening in the diaphragm 24, as occurs in a sliding hiatal hernia. The ring 10 fits snugly around the esophagus 30 in order to prevent such migration.

As shown in FIGS. 2 and 3, the ring 10 incorporates a radiopaque marker 40 about its inner circumference. The radiopaque marker 40 permits visualization of the ring 10 intraoperatively and postoperatively to ensure that the patch 9 is properly positioned during surgery, and that the patch 9, and particularly the ring 10, maintains its position postoperatively in order to properly strengthen and reinforce the EG junction. The radiopaque marker 40 may be any conventional marker known in the art for allowing radiographic visualization of a prosthesis, and may comprise a radiopaque dye; a metal wire molded into the ring 10 made from a biocompatible material, such as titanium, tantalum, stainless steel, or nitinol; or metallic salts (such a barium compounds) embedded in the synthetic biocompatible material from which the patch 9 is formed.

Figure 4:
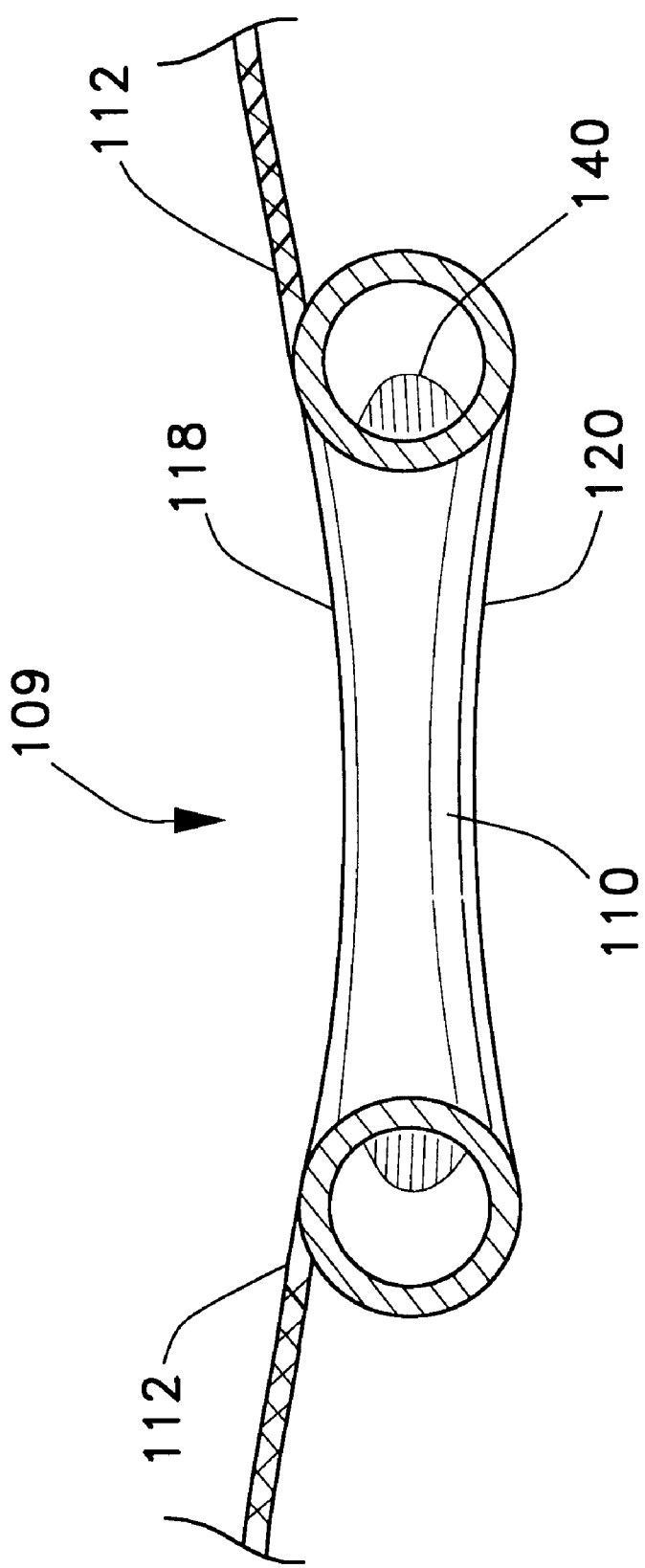
FIG. 4 is a section view of an alternative embodiment of a hiatal hernia repair patch according to the present invention.

As shown in FIGS. 2 and 3, in a first embodiment the ring 10 has the shape of a torus in which the toroidal body is solid. FIG. 4 shows a second embodiment of the patch, referred to generally as 109, in which the toroidal body of the ring 110 is hollow. The mesh 112 extends from the superior side 118 of the ring 112 and the ring 112 has an inferior side 120 and a radiopaque marker 140 about its inner circumference, as described above in connection with the first embodiment of the patch 9. Although the shape of a torus, and therefore a substantially circular cross-section, is preferred, it will be understood that the scope of the invention extends to a patch having a ring, regardless of the sectional shape of the ring, which may be flat, as shown by the ring 210 shown in FIG. 5 so that its cross-sectional shape is rectangular or C-shaped in vertical section, or any other shape. Further, it will be understood that while it is preferred that the mesh 12, 112, or 212, extend from the superior side 18 or 118 of the ring 10, 110 or 210, since this orientation places the mesh 12, 112 or 212 closer to the diaphragm 24 and provides better support for the EG junction 26, it will be understood that the mesh 12, 112, or 212 may alternatively extend from the ring 10, 110, 210 medially or from the inferior side 20 or 120. Other than the cross-sectional shape of the ring, the embodiments shown in FIGS. 4 and 5 are otherwise substantially identical to the embodiment shown in FIGS. 1–3.

Implanting the hiatal hernia patch involves several steps. The hiatal hernia is dissected laparoscopically or by open technique, mobilizing the stomach and lower esophagus out of the hiatal hernia using blunt and sharp dissection. The esophago-gastric junction is dissected circumferentially. The hiatal hernia patch 9, 109 or 209 is placed around the esophago-gastric junction 26. Prior to implantation the ring 10, 110 or 210 must be checked to verify that it is generally larger than the patient's distal esophagus 30. A 60 French blunt tip esophageal bougie should be inserted through the patient's mouth into the esophageal lumen after mobilization of the distal esophagus and the stomach out of the hiatal hernia sac to ensure the ring fits snugly outside the esophagus. The ring must fit snugly. If the ring's aperture is too large, the ring will be ineffective at preventing the stomach's migration; if the ring's aperture is too small the esophagus will become partially obstructed.

The next step requires trimming the patch's biocompatible mesh 12 so that the mesh generally conforms to the shape and size of the patient's diaphragm. In the alternative, the manufacturer can produce the patch in a variety of shapes and sizes. The physician can select one, from an assortment, that conforms to the shape and size of the patient's diaphragm.

Figure 6:
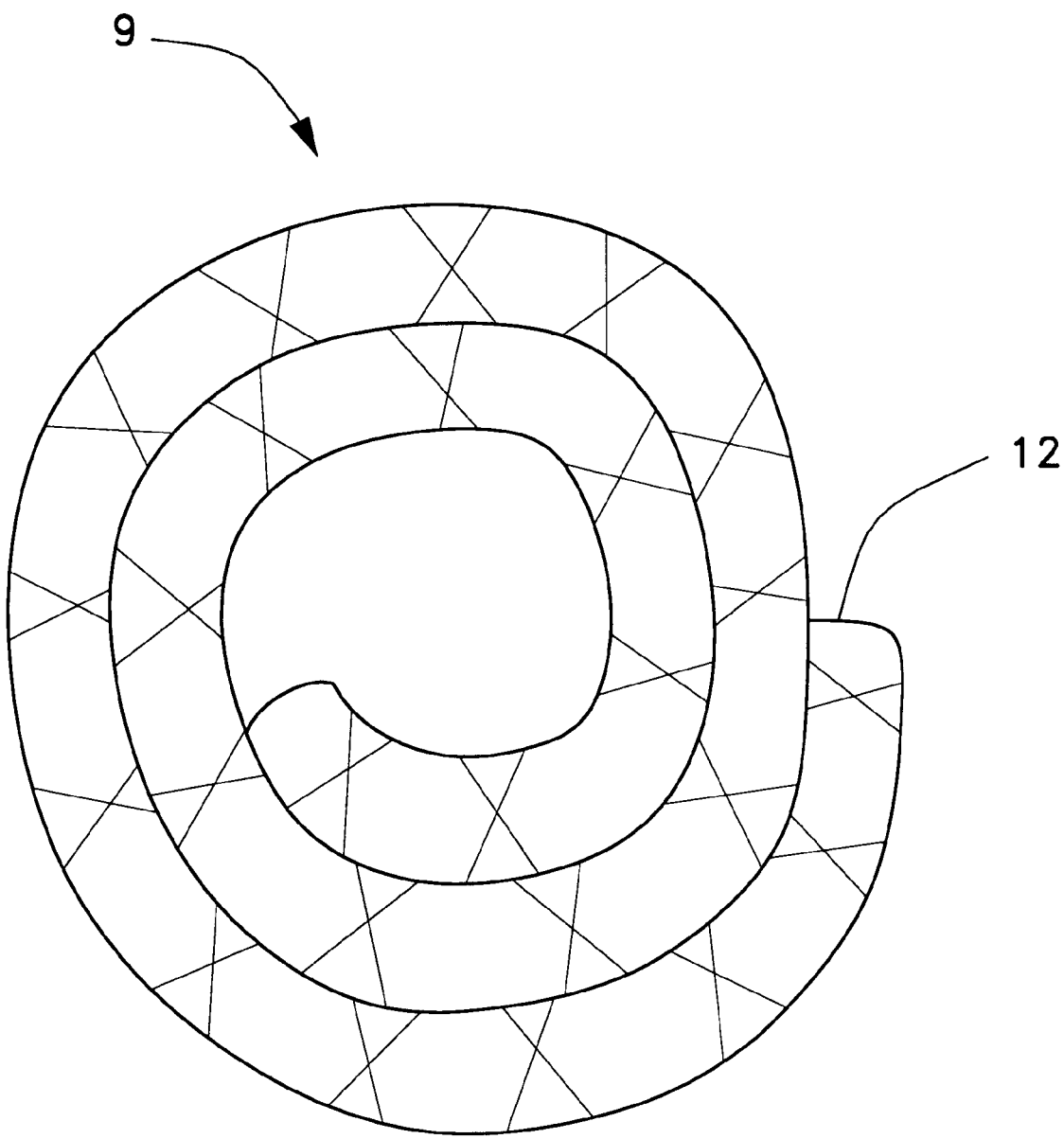
FIG. 6 is an end view of a hiatal hernia repair patch according to the present invention folded for insertion through a laparoscopic port.

The prothesis is t hen placed around the patient's esophagus. The slit 14 in the prothesis allows for its placement. The ring and mesh may be made of flexible polypropylene, which also aids in placement through small, laparoscopic incisions, or through laparoscopic ports. The patch 9 may be folded, as shown in FIG. 6, for insertion through a laparoscopic port. The patch 9, however, is resilient enough that it regains its shape after insertion through the incision.

Finally, the physician secures the patch 9 to the edges of the hernia defect and the undersurface of the diaphragm using a stapling device or sutures of nonabsorbable material, bridging the hiatal hernia defect. FIG. 5 illustrates an environmental view of the prothesis once it has been put in place, and prior to its attachment to the diaphragm. The procedure of implanting the patch may be performed using laparoscopic techniques. The patch may be viewed radiographically either intraoperatively or postoperatively to ensure proper placement of the ring about the distal esophagus.

It is to be understood that the present invention is not limited to the sole embodiments described above, but encompasses any and all embodiments within the scope of the following claims.

I claim:

1. A hiatal hernia repair patch, comprising:
    a ring defining an opening, the opening being sized and dimensioned for encircling a patient's distal esophagus, the ring having a slit extending radially through the ring; and
    at least one section of biocompatible mesh, said mesh extending radially from said ring.

2. The hiatal hernia repair patch according to claim 1, wherein said at least one section of biocompatible mesh is a single section of mesh extending radially from said ring substantially 360° about the circumference of said ring, said mesh having a slit extending radially through said mesh in registry with the slit extending through said ring.

3. The hiatal hernia repair patch according to claim 1, wherein said ring has the shape of a torus, said ring having a superior side and an inferior side.

4. The hiatal hernia repair patch according to claim 3, wherein said mesh extends from the superior side of said ring tangential to the ring.

5. The hiatal hernia repair patch according to claim 3, wherein said ring is solid.

6. The hiatal hernia repair patch according to claim 3, wherein said ring is hollow.

7. The hiatal hernia repair patch according to claim 1, further comprising a radiopaque marker incorporated into said ring and disposed about the circumference of said ring.

8. The hiatal hernia repair patch according to claim 1, wherein said patch is made from a flexible biocompatible material.

9. The hiatal hernia repair patch according to claim 1, wherein said patch is made from polypropylene.

10. A method for implanting the hiatal hernia repair patch of claim 1, comprising the steps of:
    (a) dissecting a hiatal hernia, including mobilizing a patient's stomach and lower esophagus out of the hiatal hernia sac using blunt and sharp dissection;
    (b) dissecting the patient's esophago-gastric junction circumferentially;
    (c) placing the patch around the patient's esophagus; and
    (d) attaching the mesh to an edge of the hiatal hernia defect and to an undersurface of the patient's diaphragm, bridging the hiatal hernia defect.

11. The method of implanting a hiatal hernia repair patch according to claim 10, further comprising the step of verifying that the ring is generally larger than the diameter of a specific patient's distal esophagus before placing the patch around the patient's esophagus.

12. The method of implanting a hiatal hernia repair patch according to claim 10, further comprising the step of inserting an esophageal bougie through the patient's mouth into the esophageal lumen after mobilization of the distal esophagus and the stomach out of the hiatal hernia sac in order to ensure that the ring fits snugly outside the esophagus.

13. The method of implanting a hiatal hernia repair patch according to claim 10, further comprising the step of trimming the mesh so that said mesh conforms generally to the shape and size of the patient's diaphragm.

14. The method of implanting a hiatal hernia repair patch according to claim 13, wherein the step of trimming the mesh is performed during the manufacturing of the prosthesis, and wherein said method further comprises the step of selecting the prosthesis of a proper size from a plurality of prostheses with variously sized mesh.

15. The method of implanting a hiatal hernia repair patch according to claim 10, wherein the steps of dissecting the hiatal hernia and placing the patch about the patient's esophagus are performed using an open technique.

16. The method of implanting a hiatal hernia repair patch according to claim 10, wherein the steps of dissecting the hiatal hernia and placing the patch about the patient's esophagus are performed using a laparoscopic technique.

17. The method of implanting a hiatal hernia repair patch according to claim 16, further comprising the steps of:
    (a) inserting a laparoscopic port through the patient's abdomen;
    (b) folding the patch into an elongated tubular shape;
    (c) inserting the folded patch through the laparoscopic port; and
    d) unfolding the patch in order to place the patch about the patient's distal esophagus.

18. The method of implanting a hiatal hernia repair patch according to claim 10, further comprising the step of verifying proper placement of the patch about the patient's distal esophagus by radiographic imaging.

* * * * *